United States Patent [19]

Jurgens, Jr. et al.

[11] Patent Number: 5,316,772
[45] Date of Patent: May 31, 1994

[54] BILAYERED ORAL PHARMACEUTICAL COMPOSITION WITH PH DEPENDENT RELEASE

[75] Inventors: Raymond W. Jurgens, Jr., Roswell; Roger D. Graben, Powder Springs; Adnan S. Sabir, Marietta, all of Ga.

[73] Assignee: Solvay & Cie, S.A. (Societe Anonyme), Brussels, Belgium

[21] Appl. No.: 801,358

[22] Filed: Dec. 2, 1991

Related U.S. Application Data

[63] Continuation-in-part of Ser. No. 649,707, Dec. 19, 1990, abandoned.

[51] Int. Cl.⁵ .......................... A61K 9/24; A61K 9/58; A61K 9/62; A61K 9/16
[52] U.S. Cl. ......................... 424/472; 424/471; 424/494; 424/495; 424/497; 424/461; 424/462
[58] Field of Search ............... 424/471, 472, 494, 495, 424/497, 461, 462; 514/867

[56] References Cited

U.S. PATENT DOCUMENTS

| | | | |
|---|---|---|---|
| 3,431,338 | 3/1969 | Munzel | 424/471 |
| 4,432,966 | 2/1984 | Zeitoun et al. | 424/471 |
| 4,780,318 | 10/1988 | Appelgren et al. | 424/469 |
| 4,863,742 | 9/1989 | Panoz et al. | 424/472 |
| 4,904,474 | 2/1990 | Theeuwes | 424/490 |
| 4,980,173 | 12/1990 | Halskov | 424/490 |

FOREIGN PATENT DOCUMENTS

| | | |
|---|---|---|
| 0247983 | 12/1987 | European Pat. Off. |
| 0366621 | 5/1990 | European Pat. Off. |
| WO83/00435 | 2/1983 | PCT Int'l Appl. |
| WO91/07172 | 5/1991 | PCT Int'l Appl. |

Primary Examiner—Edward Webman
Attorney, Agent, or Firm—Willian Brinks Hofer Gilson & Lione

[57] ABSTRACT

An oral pharmaceutical composition comprises a core containing a drug, a first inner layer coating on the core which contains a drug, and a second inner layer coating on the first inner layer coating which also contains drug. This oral pharmaceutical composition is used especially for treating intestinal diseases.

55 Claims, 1 Drawing Sheet

BILAYERED ORAL PHARMACEUTICAL COMPOSITION WITH PH DEPENDENT RELEASE

This is a continuation of application Ser. No. 07/649,707 filed Dec. 19, 1990 now abandoned.

BACKGROUND OF THE INVENTION (1) Field of Invention

The present invention relates to an oral pharmaceutical composition. In particular, the present invention relates to an oral pharmaceutical composition that acts to deliver drug throughout the small and large bowel.

(2) Prior Art

In the pharmaceutical arts it is often desirable to prevent the dissolution of drugs within the stomach. This may be to protect the stomach from the irritating effects of the drug or to protect the drug from being chemically degraded by the gastric juices of the stomach. This is routinely accomplished by applying enteric (gastric resistant) coating materials which allow drug dissolution to occur in the small intestine, the large intestine, or a portion of the small or large intestine. For example, in U.S. Pat. No. 4,780,318 an oral pharmaceutical composition is disclosed which comprises a core containing the active therapeutic compound and a carrier, a diffusion membrane, an outer layer and a flavored or colored layer applied outside. In that way the active compound begins to release only in the colon and not in the small bowel; however, this composition does not uniformly expose both bowels to the drug. Moreover, no current method exists which allows uniform and complete exposure of both the small and large intestine to drug while at the same time preventing dissolution of the drug in the stomach. No commercially available drug preparation is known to applicants that delivers drug at the low pH ranges that exists in the upper intestinal tract, and also in the lower intestinal tract and colon in the same dosage form.

SUMMARY OF THE INVENTION

It is an object of the present invention to provide an oral pharmaceutical composition which enables constant drug delivery to both the small and large bowel areas ("or small and large intestine and which dissolves continuously in both the small and large bowel.

Another object of the present invention is to provide for an oral pharmaceutical composition for treating an intestinal disease.

Another object of the present invention is to provide a method for achieving the release of an orally administered drug in the small and large bowel which comprises administering an oral pharmaceutical composition according to the invention.

Another object of the present invention is to provide a process for treating an intestinal disease orally which comprises administering an oral pharmaceutical composition according to the invention.

Another object of the present invention is to provide an oral pharmaceutical composition specific for release into the small and large bowel in the same formulation and dosage form.

Another object of the present invention is to provide a method for the treatment of mammals, including man, by the oral administration of a therapeutically active dose of a drug, wherein the drug is administered in the form of the pharmaceutical composition prepared according to the invention.

According to this invention an oral pharmaceutical composition is disclosed comprising a core, a first inner layer coating on the core, and a second inner layer coating on the first inner layer coating wherein the core, the first inner layer coating and the second inner layer coating contain a drug, the composition acting to deliver the drug to both small and large bowel areas. Alternatively, the first inner layer coating may contain no drug. Also the formulation may contain an external layer with or without a drug.

Also according to the invention, a method for achieving the release of an orally administered drug in the small and large bowel is disclosed which comprises administering an oral pharmaceutical composition comprising a core, a first inner layer coating on the core, and a second inner layer coating on the first inner layer coating, wherein the core, the first inner layer coating and the second inner layer coating contain a drug.

Also according to the invention is a method of making an oral pharmaceutical composition comprising the steps of mixing a drug and a pharmaceutically acceptable excipient and compressing the mixture to form a core, mixing the components of a first inner layer coating comprising a first coating agent and a drug and applying the first inner layer coating to the core, drying the coated core, mixing the components of a second inner layer coating comprising a second coating agent and a drug, and applying the second inner layer coating to the coated core, and drying the twice coated core.

Preferably, the composition according to the invention is formulated in the form of a tablet. Also preferably, the composition according to the present invention contains a first inner layer coating which contains drug and which releases the drug at a pH of 5 through 8, and a second inner layer coating which releases the drug at of pH of 3 through 6.

Usually, the composition comprises a concentration of drug in the core of from 20–60% by total drug weight, a drug concentration in the first inner layer coating of 15–45% by total drug weight, and a drug concentration in the second inner layer coating of 15–45% by total drug weight. Preferably, the first inner layer coating is composed of either acrylic resins, cellulose derivatives or a blend of these compounds, and the second inner layer coating comprises cellulose derivative or polyvinyl acetate phthalate. Most preferably, the second inner layer is comprised of either ethylcellulose modified with hydroxypropylmethylcellulose, or polyvinyl acetate phthalate.

An advantage of the present invention is to provide an oral pharmaceutical composition that does not dissolve in or release the drug in the stomach, allowing the drug to be released uniformly into the entire intestinal area.

Another advantage of the present invention is to provide an oral pharmaceutical composition that can be utilized for gastrointestinal diseases that affect or potentially could affect both parts of the bowel, where exposure to drug therapy is required along the entire length of the bowel.

Another advantage of the present invention is to provide for better patient compliance due to fewer tablets needed to accomplish the same goal, i.e. dispersion throughout the entire gastrointestinal tract of a selected drug.

Another advantage of the present invention is to provide for a method which enables the continuous administration of a low potency drug throughout the large and small bowel.

DETAILED DESCRIPTION

Figure 1:
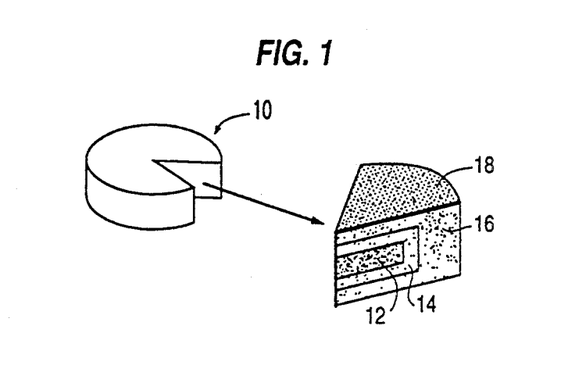
FIG. 1 represents a cross sectional view of an oral pharmaceutical preparation prepared in accordance with this invention.

As shown in FIG. 1, the present invention relates to an oral pharmaceutical composition comprising a drug having at least a core, 12 a first inner layer coating 14 on the core, a second inner layer coating 16 on the first inner layer coating and an external layer 18 wherein the core, the first inner layer coating and the second inner layer coating contain drug. Preferably, the composition is formulated in the form of a tablet, although other embodiments can be conceived, e.g., in the form of pellets or tablets in a capsule.

The drug contained in the oral pharmaceutical composition according to the invention can be any drug or medicament known for its therapeutic effect on intestinal disease. The composition according to the invention can consist of one or several drugs, either in combination and dispersed throughout each layer, or with separate drugs in the core, the first layer, and the second layer, acting to deliver a different drug to different parts of the bowel.

Generally, the drug is used for treating an intestinal or enteric disease. Preferably, the drug is used for treating a bowel complaint, for example, inflammatory bowel diseases including the group of disorders characterized by acute and chronic inflammation in all parts of the small and large intestines, ulcerative or non-ulcerative colitis, Crohn's disease, idiopathic proctitis, arthritis, regional enteritis, stoppage of bowel, peritonitis, and diarrhea.

In Crohn's disease, disease activity and histological changes can be noted from high up in the intestinal tract, e.g., in the area just past the pyloric sphincter, down to the anorectal area. As indicated, supra, this longitudinal distance represents a change in pH of from 3–8. The unique delivery system of this invention will enable drug to be delivered throughout this wide pH range. Some examples of particular drugs used in treating inflammatory bowel diseases are 5-aminosalicylic acid or a pharmaceutically acceptable salt or ester thereof, salicylates, indomethacin, steroids (such as hydrocortisone, prednisone, prednisolone, beclomethasone), salicylazosulfapyridine, pipenzolate bromide, silicium oxide, bismuth oxide, aluminum oxide, magnesium oxide, sodium oxide and digestive enzymes or a blend of two or several of these drugs. Preferably, the drug according to the invention is 5-aminosalicylic acid or a pharmaceutically acceptable salt or ester thereof.

The concentration of drug in the composition according to this invention will be known or readily ascertainable by those skilled in the art. Literature sources for these dosages would include references such as: E. R. Barnhart, *Physicians' Desk Reference*, 45th ed. Medical Economics Data, Oradell, N.J., 1991; and A. G. Gilman, T. W. Rall, A. S. Nies, P. Taylor, *Goodman and Gilman's The Pharmacological Basis of Therapeutics*, 8th ed. Pergamon Press, New York, 1990, as well as other common medical and pharmacology texts. For drugs under development these concentrations would be determined by one skilled in the art from the results of clinical studies. In many cases the concentration of drug could be less than conventional doses due to the unique characteristics of the present invention wherein the drug is delivered to the specific location where needed.

The core according to this invention is comprised of drug as well as inactive ingredients (excipients) added to influence or enhance the properties of the core. These excipients or inactive materials and the manufacturing processes employed to produce the core are those typically used in the field. These excipients and processes may often be found in the literature references such as: A. R. Gennaro, *Remington's Pharmaceutical Sciences*, 18th ed. Mack, Easton, Pa., 1990; L. Lachman, H. A. Lieberman, and J. L. Kanig, *The Theory and Practice of Industrial Pharmacy*, Lea & Febiger, Philadelphia, 1986; and J. C. Boylan, J. Cooper, and Z. T. Chowhan, *Handbook of Pharmaceutical Excipients*, American Pharmaceutical Association, Washington, 1986. These excipients may include diluents such as sorbitol, mannitol, lactose, starch, cellulose, sucrose, and calcium salts, and the like; flow aids such as talc, silica, and metallic stearates; lubricants such as magnesium stearate, calcium stearate, zinc, stearate, polyethylene glycol, wax, vegetable oil, and the like; inorganic salts such as potassium chloride, sodium chloride, and the like; as well as surfactants such as sodium lauryl sulfate and dioctyl sodium sulfosuccinate. These excipients could also include disintegrants such as sodium starch glycolate, crospovidone, modified cellulose, and the like; as well as antioxidants such as potassium metabisulfite, ascorbic acid and others.

The concentration of drug in the core 12 (as a percentage of total drug concentration) is generally 20–60% by weight of total drug (20–60 mg per 100 mg of total drug weight), and preferably 30–50% by weight of total drug.

The first inner layer coating 14 on the core comprises at least one or several coating agents and may or may not contain a drug. Usually, the first inner layer coating agent is selected from the group comprising acrylic resins, polysaccharides, cellulose derivatives, sugar derivatives or mixtures of these compounds. Preferably, the coating agents are acrylic resins, and cellulose derivatives, or a blend which includes these compounds. Suitable acrylic resin coating agents include polyacrylates. Polymers and copolymers of the following compounds are examples of such suitable polyacrylates: polymethacrylate, polyethacrylate, methacrylic acid, methacrylic acid methyl ester, methyl methacrylate and trimethylammonium ethylmethacrylate chloride, their co- and ter- polymers and derivatives thereof. Mixtures of these polyacrylate compounds have also been found to be suitable. Acrylic resin preparations are available under the various EUDRAGIT ® products, including polyethyl acrylate, methyl methacrylate and trimethylammonium ethylmethacrylate chloride copolymer. An example of a suitable cellulose derivative is a compound chosen from the hydroxymethylcellulose acetate-succinates.

The first inner layer coating 14 may also comprise a pharmaceutically acceptable excipient (see e.g., supra, discussion regarding the core), or other additives, for example, plasticizers such as polyethylene glycol, triethyl citrate, triacetin, dibutyl phthalate; opacifiers and extenders such as talc and titanium dioxide, and solvents used to apply the coating agents and additives such as water, alcohols, acetone, methylene chloride, phthalic acid derivatives and other organic solvents.

Preferably, the first inner layer coating 14 according to the invention releases drug at pH 5 through 8. However, a first inner layer coating that releases drug at pH 6 through 8 is acceptable. Also preferably, the first inner layer coating agent has the characteristic to break up, modify its structure or dissolve at this pH. The pH 5–8 range would be effective in treating diseases of the lower bowel such as ulcerative colitis.

The concentration of drug in the first inner layer coating 14 is generally 15–45% by weight of total drug, and preferably 30% by weight of total drug.

The second inner layer coating 16 comprises at least a drug and one or several coating agents different from the coating agent of the first inner layer coating. It is important that the coating agents of the first and second inner layers be designed to release drug at different pHs, and thus, these layers will generally be composed of different coating agents. Also it may comprise select pharmaceutically acceptable excipients which can consist of one or several coating compounds known in this field. These excipients are described, supra, in the discussion of the core. The second inner layer coating can also contain a plasticizer, for example, polyethylene glycol, dibutyl phthalate, triacetin or triethyl citrate.

Usually, the second inner layer coating agent comprises either a cellulose derivative or polyvinyl acetate phthalate ("PVAP"). Examples of suitable cellulose derivatives are cellulose esters, ethylcellulose or hydroxypropylmethylcellulose phthalate. Preferably, either ethylcellulose modified with hydroxypropylmethylcellulose, or polyvinyl acetate phthalate is used as the coating agent of the second inner layer coating. The second inner layer coating agent may also be modified polyvinyl acetate phthalate. It is an object of this formulation to modify the integrity of the second inner layer coating and thereby allow for release of drug in the low pH ranges. The principle of the second inner layer coating is to allow break down of the integrity of a weakened or modified enteric coating through intestinal fluid penetration of the coating.

The second inner layer coating 16 according to the invention preferably releases drug at a pH of 3 though 6, however release at a pH of 4 through 6 is also acceptable. Preferably, the coating agent of this second inner layer coating has the characteristic to break up, to modify its structure or to dissolve at this pH range.

The concentrations of drug in the second inner layer coating 16 are generally 15–45% by weight of the total drug, preferably 30% by weight.

The optional external layer 18 according to the invention is a layer equivalent to the second inner layer coating except no drug need be added. The external layer can include flavoring or coloring agents. The ratio of weight between the core and the external layer is comprised generally between 0.4 and 0.1.

The pH values at which the first and second inner layer coatings release drug can be adjusted depending upon where along the intestinal tract drug therapy is desired. In general, where the second inner layer coating releases at pH 3 through 6 and the first inner layer coating releases at pH 5 through 8, and drug is included in the core, first inner layer coating and second inner layer coating, drug will be administered over the length of the small and large bowel. It is contemplated that the present invention includes administration of drug along the entirety of the small and large bowel, as well as the more specific intermittent administration of drug to locations along the tract, from a single tablet or equivalent formulation. The latter type of administration could be carried out, for example, by including drug only in the core and the second inner layer coating, thereby affording non-continuous but pH specific administration of drug to the small and large bowel with a single tablet or equivalent formulation. This procedure could be extended to multiply layered drugs by repetitive application of layer coatings. By including drug in the coating themselves the present invention allows for the continuous administration of a drug which requires a relatively large dosage, e.g., a drug with relatively low potency, along the entire length of the small and large bowel. This is a desired result for some drugs wherein a relatively instantaneous release of drug upon reaching a specific pH level in the gastro-intestinal tract would not be as effective as continuous administration.

Moreover, the drug absorption pattern of a particular drug in dependent on several factors. The change in pH from the pyloric sphincter to the anorectal area can be taken advantage of to formulate a composition that breaks apart at a certain pH. There is also erosion due to the passage of the tablet through the intestinal tract. Finally, there may be patient specific factors that contribute in various ways to the absorption of drug. The present invention takes advantage of both pH and erosion in administering drug along the length of both the small and large bowel.

The process for preparing the oral pharmaceutical composition according to the invention comprises the following steps:
preparation of the core;
coating the core to form the first inner layer;
coating the coated core to form the second inner layer;
optionally coating the twice coated core to form the external layer.

Generally the drug and the pharmaceutically acceptable excipient are mixed until a homogeneous dispersion results.

In order to make a tablet:
a homogeneous blend is compressed to form the core;
the core of the composition according to the invention is placed in a rotatable coating pan, or fluid bed apparatus;
the components comprising the separate inner layer coatings, e.g., drug, coating agent, pharmaceutically acceptable excipient and other additives are mixed homogeneously;
the mixed components of the first inner layer coating are introduced in the coating pan or fluidized bed unit by spraying, the pan is rotated or the tablet bed suspended to provide the tablets with a thin and uniform coat of the composition comprising the first inner layer coating and the coated cores subsequently dried;
this operation is repeated on the dried tablets with the mixed components of the second inner layer coating; and
the components of the external layer are applied.

The invention is illustrated by the examples which follow.

EXAMPLE 1

(1) Preparation of the Core 6,400 g of milled potassium chloride is mixed with 40,000 g of 5-aminosalicylic acid for 5 minutes under ambient temperature (20°–25° C.). This blended combination is passed through a hammer forward Fitzmill and reblended for 4 minutes. 16 g of potassium metabisulfite and 3,200 g of povidone are dissolved in RDI water (10,000 g) as a binder solution. The binder solution is then mixed with the blended combination containing 5-aminosalicylic acid at 5–15 minutes at ambient temperature (20–°25° C.). The wet mass so obtained is passed through a hammer forward Fitzmill perforated band (¾ inch, or 1.9 cm) at high speed. Then the wet mass is spread on trays, and cried for 16 hours at 60° C. and atmospheric pressure. The dried mass is again milled and placed into a mixer with 6,400 g of sorbitol, which was previously milled through a Fitzmill, knives forward.

1,600 g of a screened mixture consisting of a combination of 94% by weight calcium stearate NF and 6% by weight sodium lauryl sulfate NF is added into the mixer. This is mixed for 8–10 minutes at ambient temperature (20°–25° C.). 160 g of sodium starch glycolate which has been previously passed through a 40 mesh screen and preblended with 0.8 kg of the calcium stearate-sodium lauryl sulfate mixture is added into the mixer. This combination is mixed for approximately 5 minutes at ambient temperature and compressed into tablet form. The tablet cores so obtained have a weight of 3.0 to 5.0 g for 10 cores, a hardness of 12 to 20 kg, a thickness of 0.12 to 0.16 inches, and a friability of NMT 0.3%, and a dissolution of at least 50% in 95 to 105 minutes in a pH range of from 6 to 8.

(2) The First Inner Layer Coating

A solution of 97,500 ml of alcohol (SDA-3A) and 40,870 ml of methylene chloride is prepared and mixed. In a low shear mixer, the alcohol and methylene chloride solution is combined with 1630 g of dibutyl phthalate and 30,000 g of methacrylic acid copolymer NF type B (EUDRAGIT ® S-100, a trademark of Rohm Pharma). 30,000 g of 5-aminosalicylic acid is added into the mixture. This solution is mixed at ambient temperature until a homogeneous coating preparation results. The tablet cores obtained from the first step are then placed in an Accela-Cota coating pan. The cores are then warmed to 30°–35°. The coating preparation is then sprayed onto the warmed cores using a low shear pump at a pressure of 30–70 psi with an exhaust temperature of 30°–35° C. being maintained. This preparation is applied until a tablet weight gain of approximately 40–50% is obtained, dependent upon the desired dissolution profile. The tablets so obtained are then dried at an exhaust temperature of 30°–35° C. for 30–60 minutes at atmospheric pressure. This formulation is designed to result in drug release at pHs of greater than 6.

(3) The Second Inner Layer Coating 30,000 g of 5-aminosalicylic acid is thoroughly dispersed in approximately 30,000 g of ethylcellulose modified with hydroxypropylmethylcellulose in a high shear mixer at ambient temperature. 90 g of a plasticizer (PEG 400) is added during the mixing until a homogeneous coating preparation is obtained. The tablets with the dried first inner layer coating are placed in an Accela-Cota coating pan. These tablets are warmed to 30°–35° C. The coating preparation is sprayed onto the warmed cores using a low shear pump at a pressure of 30–70 psi with an exhaust temperature of 30°–35° C. It is sprayed on until a tablet weight gain of 40–50% is obtained. The tablets so obtained are then dried at an exhaust temperature of 30°–35° C. for 30–60 minutes at atmospheric pressure. This formulation is designed to result in drug release at pHs greater than 4.

(4) The External Layer

A thin coating identical in composition to the second inner layer coating except with no drug added is sprayed onto the dried tablets as described, supra, for the second inner layer coating. This procedure should increase the total weight by another 4–10%.

EXAMPLE 2

A. The core

The core tablet formulation contained 150 milligrams of mesalamine. The qualitative and quantitative composition of the core tablet is given in the Table 1.

TABLE 1

| COMPOSITION OF CORE TABLET | | |
|---|---|---|
| INGREDIENT | % W/W | MG/TABLET |
| Mesalamine (5-ASA) (Salsbury) | 69.2 | 150 |
| Potassium Chloride USP Granular | 11.1 | 24 |
| Povidone USP (Plasdone K-29/32) | 5.5 | 12 |
| Potassium Metabisulfite NF | 0.03 | 0.06 |
| Sorbitol NF/FCC Crystalline Powder | 11.1 | 24 |
| A mixture of 94% by weight calcium stearate NF and 6% by weight sodium lauryl sulfate NF | 2.8 | 6.0 |
| Sodium Starch Glycolate NP (Primojel) | 0.3 | 0.6 |
| Purified Water USP | — | — |
| TOTALS | 100 | 216.7 |

The tablet was produced by a wet granulation process. The dried lubricated granules were compressed on a Stokes B-2 sixteen station rotary tablet press using seven sets of 5/16 inch, plain, standard concave tooling. The batch size was 26 kilograms (120,000 tablets).

The cores were subjected to physical testing and the results given below.

| | |
|---|---|
| Average Tablet Weight = | 219.3 mg |
| Average Hardness = | 7.2 kg |
| Average Thickness = | 3.6 mm |
| Average Diameter = | 8.5 mm |
| Disintegration Time = (gastric fluid and simulated intestinal fluid) | 15–20 minutes |

(B) Selection of Coating Polymers and Solvents

The polymers utilized were selected based upon the pH at which they are soluble. Eudragit ® S-100 (methacrylic acid copolymer NF Type B) was chosen for the first inner layer coating since it is soluble from pH 7 upwards. Isopropyl alcohol was chosen as a solvent for this polymer. Isopropanol is a preferred solvent for this polymer.

Polyvinyl acetate phthalate ("PVAP") was chosen as the polymer for use in the second inner layer coating due to the excellent solubility of this polymer around pH 4.5, which is lower than the pH at which other commercially available enteric polymers will solubilize. Opaseal ®, a commercially available ready-to-use dispersion of PVAP in SDA-35A Alcohol, was employed in these trials. Alcohol USP was employed for further dilution of this system. An external layer was not employed in these trials. The Opaseal ® system without the drug would be useful for this purpose.

(C) The First Inner Layer Coating

The formulation selected for the first inner layer coating is as shown in Table 2:

TABLE 2

| INGREDIENT | QUANTITY (% W/W) |
|---|---|
| Methacrylic Acid Copolymer Type B NF | 2.0 |
| Triethyl Citrate, Pharmaceutical Grade | 0.3 |
| Talc USP 123 | 3.0 |
| Mesalamine (5-ASA) (Salsbury) | 11.0 (67.5% of solids) |
| Purified Water USP | 2.0 |
| Isopropyl Alcohol USP, 99% | 81.7 |
| TOTAL | 100.0 |

Seven hundred grams (3200 tablets) of cores were coated with polymer using 3000 grams of coating suspension (16.3% solid content) employing the procedure described below:

Triethyl citrate, (TEC) isopropyl alcohol, and purified water were added to a clean, dry four liter glass beaker. While stirring at a speed sufficient to create a vortex, the methacrylic acid copolymer was dispensed into the TEC-IPA-Water solvent mixture. The speed was decreased below vortex level and stirred for 30 minutes, or until a clear solution results. While stirring at high speed, a mesalamine-talc mixture was prepared and added to the solution, and the solution stirred for 15 minutes at high speed and then passed through a 60 mesh screen. Isopropyl alcohol was added to the suspension until the total weight equaled 3000 grams. Throughout the coating process, the solution was stirred with a magnetic stirrer.

The coating was performed as follows:

The Hi-Coater and tablets were preheated to an outlet temperature of 30°-32° C. The suspension was spray coated onto tablets according to the target parameters listed below:

| Pan Speed = | 21 rpm |
|---|---|
| Pump Speed = | 70 rpm (delivery rate equals approximately 17 grams/minute) |
| Inlet Temperature = | 44° C. |
| Outlet Temperature = | 30–32° C. |
| Atomizing Air Pressure = | 1.8 kg/cm² |
| Approximate Coating Time = | 3 hours |

The tablets were then tray dried in a convection oven at 40° C. for approximately 16 hours.

(D) Second Layer Composition

The formulation selected and employed for the second inner coating layer is listed in Table 3:

TABLE 3

| INGREDIENT | (% W/W) |
|---|---|
| Mesalamine | 11.0 |
| Talc USP 123 | 3.0 |
| Triethyl Citrate | 0.5 |
| Opaseal ® (30% solids) | 6.7 (2% solids & 4.7% solvents) |
| Alcohol USP | 78.8 |
| TOTAL | 100.0 |

Approximately 900 grams of first inner layer coated tablets were coated with polymer in 3000 grams of the above formulation employing the process described below. The mesalamine and talc were mixed in a plastic bag and triethyl citrate and Opaseal ® were added to a clean, dry four liter glass beaker. The mesalamine-talc mixture was added to beaker containing Opaseal ®-TEC and mixed for one minute at 3000–4000 rpm. Alcohol was added and mixed at 3000–4000 rpm for 15 minutes and the suspension passed through a 60 mesh screen. Alcohol was added until the total weight equaled 3000 grams. Throughout the coating process, the mixture was stirred with a magnetic stirrer.

Coating

The Hi-Coater and tablets were preheated to an outlet temperature of 30°-32° C. The suspension was spray coated onto tablets according to the target parameters listed below:

| Pan Speed = | 21 rpm |
|---|---|
| Pump Speed = | 60 rpm (coating suspension delivery rate equals approximately 14 grams/minute) |
| Inlet Temperature = | 46–50° C. |
| Outlet Temperature = | 30–32° C. |
| Atomizing Air Pressure = | 1.8 kg/cm₂ |
| Approximate Coating Time = | 3.6 hours |

EXAMPLE 3: DISSOLUTION TESTING

Six tablets prepared according to the preceding example and known to be equivalent in weight were subjected to dissolution testing. The method employed is described below:

Apparatus:—Vanderkamp VK-6000 six spindle Dissolution Tester

Paddles, 100 rpm 900 ml media at 37° C.

Drug concentration was determined spectrophotometrically at a wavelength of 304 nm employing a Hewlett Packard Model 8451A Spectrophotometer.

Samples were withdrawn manually and filtered with the media replaced.

The finished product is described by the data in the Table 4. The dissolution media employed is described in Table 5.

TABLE 4

| PARAMETER | CORE | FIRST LAYER | SECOND LAYER | COLUMN TOTAL |
|---|---|---|---|---|
| Average Tablet Weight (mg)* | 219 (1.3) | 330 (15) | 469 (33) | N/A |
| Average Tablet Thickness (mm)* | 3.6 (0.1) | 5.0 (0.1) | 5.5 (0.2) | N/A |

TABLE 4-continued

| PARAMETER | CORE | FIRST LAYER | SECOND LAYER | COLUMN TOTAL |
|---|---|---|---|---|
| Average Tablet Diameter (mm)* | 8.5 (0.0) | 9.7 (0.1) | 10.4 (0.1) | N/A |
| Average Weight of Coated Layer (mg) - (% gained) | — | 111 (50.68%) | 139 (63.47%) | N/A |
| Theoretical Percent Mesalamine Content | 69.2 | 67.5 | 50.2 | N/A |
| Mesalamine Content** | 151.5 | 74.9 | 69.8 | 296.2 |
| Percent of Total Mesalamine | 51.1 | 25.3 | 23.6 | 100 |

*Reported as mean (standard deviation), n = 20.
**(Theoretical Percent Mesalamine Content/100) (Average Weight)

TABLE 5

DISSOLUTION MEDIA EMPLOYED

| TIME | MEDIA |
|---|---|
| 0–1 Hour | Simulated Gastric Fluid w/o enzymes, pH 1.2 (USP XXII) |
| 1–2 Hours | pH 4 Acid Phthalate Buffer (USP XXII) |
| 2–4 Hours | pH 6 Phosphate Buffer (USP XXII) |
| 4–10 Hours | Simulated Intestinal Fluid, pH 7.5 (USP XXII) |

Figure 2:
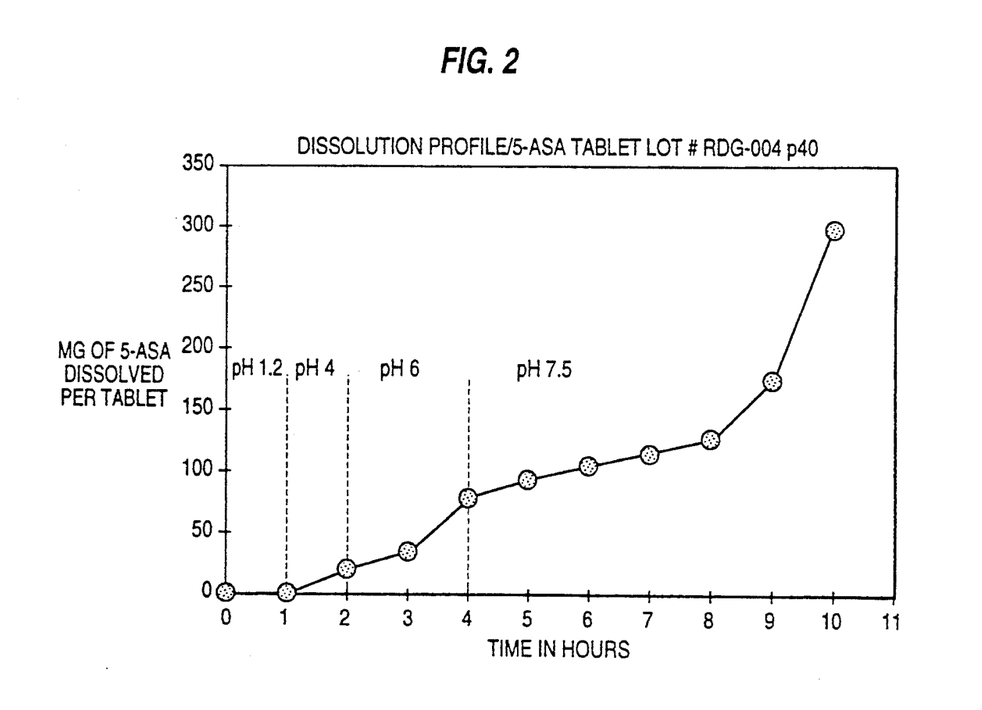
FIG. 2 is a graphical representation of the pH dissolution profile of an oral pharmaceutical preparation prepared in accordance with this invention.

Dissolution results are presented in Table 6 as well as presented graphically in FIG. 2. The data was corrected by subtracting the cumulative amount released at one hour from the cumulative amount released at later time points. The amount (36.2 mg) released at one hour is assumed to be due to absorbance 15 by inactive ingredients. This correction is strongly supported by the close agreement between the cumulative amount released at ten hours (297.9 mg) and the theoretical finished product mesalamine content (296.2 mg).

As desired, no drug was released after one hour in simulated gastric fluid. A small amount of drug (21.8 mg) was released after an hour (total time=two hours) in pH 4 buffer. Drug release continued at pH 6 and 79.5 mg of drug was released at the four-hour time-point. This is slightly more than the theoretical content (69.8 mg) of the second (outermost) layer. Drug release continues at pH 7.5 in an almost linear fashion from the four-hour to the eight-hour time-point. A large amount of drug is (35–45%) is released between eight-hour and ten-hour time-points. This is assumed to be representative of the drug contained in the core.

TABLE 6

DISSOLUTION TEST RESULTS
PADDLE METHOD, 100 RPM, 37° C.
Ph 1.2 (1 HR), pH 4 (1HR), pH 6 (2HR)
pH 7.5 (6 HR) (TOTAL 10 HOURS)

MILLIGRAM PER TABLET DISSOLVED

| TIME (HOUR) | pH | TAB 1 | TAB 2 | TAB 3 | TAB 4 | TAB 5 | TAB 6 | MEAN (SD) | CUMULATIVE AMOUNT ((AVERAGE) | CUMULATIVE AMOUNT (CORRECTED)* |
|---|---|---|---|---|---|---|---|---|---|---|
| 0 | 1.2 | 0 | 0 | 0 | 0 | 0 | 0 | 0 | 0 | 0 |
| 1 | 1.2 | 34.7 | 35.8 | 36.4 | 37.3 | 37.0 | 35.8 | 36.2 (2.6) | 36.2 | 0 |
| 2 | 4 | 16.9 | 21.7 | 22.2 | 23.4 | 25.1 | 21.5 | 21.8 (2.7) | 58.0 | 21.8 |
| 3 | 6 | 10.9 | 13.4 | 15.0 | 15.0 | 12.7 | 14.3 | 13.6 (1.6) | 71.6 | 35.4 |
| 4 | 6 | 54.6 | 61.1 | 55.7 | 56.0 | 61.4 | 57.4 | 57.7 (2.9) | 115.7 | 79.5 |
| 5 | 7.5 | 16.1 | 16 | 14.1 | 13.6 | 14.5 | 13.6 | 14.6 (1.1) | 130.3 | 94.1 |
| 6 | 7.5 | 25.2 | 26.5 | 26.9 | 25.2 | 26.2 | 26.1 | 26.0 (0.7) | 141.7 | 105.5 |
| 7 | 7.5 | 33.2 | 34.7 | 36.0 | 33.3 | 34.1 | 35.0 | 34.4 (1.1) | 150.1 | 113.9 |
| 8 | 7.5 | 47.2 | 48.2 | 49.8 | 47.5 | 44.6 | 49.6 | 47.8 (1.9) | 163.5 | 127.3 |
| 9 | 7.5 | 74.3 | 144.3 | 73.1 | 68.1 | 68.9 | 146.8 | 95.9 (38.5) | 211.6 | 175.4 |
| 10 | 7.5 | 205.6 | 218.5 | 221.8 | 220.4 | 222.0 | 222.2 | 218.4 (2.9) | 334.1 | 297.9 |

*CUMULATIVE AMOUNT - AMOUNT RELEASED AT 1 HOUR (36.2 MG)

It should be understood that a wide range of changes and modifications can be made to the preferred embodiment described above. It is therefore intended that it is the following claims, including all equivalents, which are intended to define the scope of the invention.

We claim:

1. An oral pharmaceutical composition comprising a core, a first inner layer coating on the core, and a second inner layer coating on the first inner layer coating, wherein the core, the first inner layer coating and the second inner layer coating each contain at least one drug, said at least one drug consisting of one or several drugs, either in combination and dispersed throughout each inner layer, or with separate drugs in the core, the first inner layer and the inner second layer, the composition effecting delivery of said at least one drug to both the small and large bowel, and the first inner layer coating comprises a coating agent consisting essentially of acrylic resin and releases said at least one drug at a pH of 5 through 8, and the second inner layer coating comprises a coating agent consisting essentially of a cellulose derivative, polyvinyl acetate phthalate, or polyvinyl acetate phthalate mixed with a plasticizer, and releases said at least one drug at a pH of 3 through 6; wherein said core comprises a concentration of said at least one drug of from 20–60%, said first inner layer coating comprises a concentration of said at least one drug of from 15–45% and a percentage of coating agent of between 12.3–48.7%, and said second inner layer comprises a concentration of said at least one drug of from 15–45% and a percentage of coating agent of between 31.6–49.9%.

2. The oral pharmaceutical composition according to claim 1, wherein the composition is in the form of a tablet.

3. The oral pharmaceutical composition according to claim 1, wherein said at least one drug comprises a therapeutic compound useful for treating intestinal disease.

4. The oral pharmaceutical composition according to claim 1, wherein the composition contains one or several drugs, either in combination and dispersed throughout each layer, or with separate drugs in the core, the first inner layer, and the second inner layer, whereby the composition effects delivery of a different drug to different parts of the bowel.

5. The oral pharmaceutical composition according to claim 1, wherein said at least one drug contained in the core and the first inner layer coating is different than said at least one drug contained in the second inner layer coating.

6. The oral pharmaceutical composition according to claim 1, wherein said at least one drug comprises salicylate, indomethacin, a steroid, salicylazosulphapyridine, pipenzolate bromide, silicium oxide, bismuth, oxide, aluminum oxide, magnesium oxide, sodium oxide, a digestive enzyme or a mixture thereof.

7. The oral pharmaceutical composition according to claim 1, wherein the steroid comprises hydrocortisone, prednisone, prednisolone, or beclomethasone.

8. The oral pharmaceutical composition according to claim 1, wherein constant drug delivery to the small and large bowel is effected.

9. The oral composition according to claim 1, wherein said at least one drug is released continuously along the length of both the small and large bowel.

10. The oral pharmaceutical composition according to claim 1, wherein said at least one drug comprises 5-aminosalicylic acid, a pharmaceutically acceptable salt thereof, or an ester thereof.

11. The oral pharmaceutical composition according to claim 1, wherein the core comprises at least one drug and a pharmaceutically acceptable excipient.

12. The oral pharmaceutical composition according to claim 11, wherein the pharmaceutically acceptable excipient comprises a flow aid.

13. The oral pharmaceutical composition according to claim 12, wherein the flow aid comprises talc, silica, or metallic stearate.

14. The oral pharmaceutical composition according to claim 11, wherein the pharmaceutically acceptable excipient comprises sorbitol, mannitol, lactose, starch, cellulose, sucrose, or calcium salt.

15. The oral pharmaceutical composition according to claim 11, wherein the pharmaceutically acceptable excipient comprises an antioxidant.

16. The oral pharmaceutical composition according to claim 15, wherein the antioxidant comprises potassium metabisulfite or ascorbic acid.

17. The oral pharmaceutical composition according to claim 11, wherein the pharmaceutically acceptable excipient comprises a lubricant.

18. The oral pharmaceutical composition according to claim 17, wherein the lubricant comprises magnesium stearate, calcium stearate, zinc stearate, polyethylene glycol, wax, or vegetable oil.

19. The oral pharmaceutical composition according to claim 11, wherein the pharmaceutically acceptable excipient comprises an inorganic salt.

20. The oral pharmaceutical composition according to claim 19, wherein the inorganic salt comprises potassium chloride or sodium chloride.

21. The oral pharmaceutical composition according to claim 11, wherein the pharmaceutically acceptable excipient comprises a surfactant.

22. The oral pharmaceutical composition according to claim 21, wherein the surfactant comprises sodium lauryl sulfate or dioctyl sodium sulfosuccinate.

23. The oral pharmaceutical composition according to claim 11, wherein the pharmaceutically acceptable excipient comprises a disintegrant.

24. The oral pharmaceutical composition according to claim 23, wherein the disintegrant comprises sodium starch glycolate, crospovidone or modified celluloses.

25. The oral composition according to claim 1, wherein the acrylic resin comprises polyacrylate.

26. The oral pharmaceutical composition according to claim 25, wherein the polyacrylate is selected from the group consisting of polymethacrylate, polyethylacrylate, polymers of methacrylic acid, copolymers of methacrylic acid, terpolymers of methacrylic acid, polymers of methyl methacrylate, copolymers of methyl methacrylate, terpolymers of methyl methacrylate, polymers of trimethylammonium ethyl methacrylate chloride, copolymers of trimethylammonium ethyl methacrylate chloride, terpolymers of trimethylammonium ethyl methacrylate chloride, their derivatives, and mixtures thereof.

27. The oral pharmaceutical composition according to claim 1, wherein the first inner layer coating releases said at least one drug at a pH of 6 through 8.

28. The oral pharmaceutical composition according to claim 1, wherein the cellulose derivative comprises ethylcellulose.

29. The oral pharmaceutical composition according to claim 28, wherein the cellulose derivative is hydroxypropylmethylcellulose.

30. The oral pharmaceutical composition according to claim 1, wherein the second inner layer coating releases said at least one drug at a pH of 4 through 6.

31. The oral pharmaceutical composition according to claim 1, wherein the first inner layer coating releases said at least one drug at pH 6 through 8 and the second inner layer coating releases said at least one drug at pH 4 through 6.

32. The oral pharmaceutical composition according to claim 1, wherein the concentration of drug in the core is from 20–60% by total drug weight, the concentration of drug in the first inner layer is from 15–45% by total drug weight, and the concentration of drug in the second inner layer is from 15–45% by total drug weight.

33. The oral pharmaceutical composition according to claim 1, wherein the concentration of drug in the core is from 30–50% by total drug weight, the concentration of drug in the first inner layer is about 30% by total drug weight, and the concentration of drug in the second inner layer is about 30% by total drug weight.

34. The oral pharmaceutical composition according to claim 1, wherein the second inner layer comprises polyvinyl acetate phthalate mixed with a plasticizer which comprises polyethylene glycol, dibutyl phthalate, triacetin or triethyl citrate.

35. The oral pharmaceutical composition according to claim 1, wherein the second inner layer comprises polyvinyl acetate phthalate mixed with triethyl citrate.

36. An oral pharmaceutical composition comprising a core, a first inner layer coating on the core, a second inner layer coating on the first inner layer coating, and an external layer, wherein the core and the second inner layer contain at least one drug, said at least one drug consisting of one or several drugs, either in combination and dispersed throughout each of the core and the second inner layer, or with separate drugs in the core and the first inner layer and the second inner layer, the composition effecting delivery of said at least one drug to the small and large bowel, and the first inner layer coating comprises a coating agent consisting essentially of acrylic resin and breaks up or dissolves at a pH of 5 through 8, and the second inner layer coating comprises a coating agent consisting essentially of a cellulose derivative, polyvinyl acetate phthalate, or polyvinyl acetate phthalate mixed with a plasticizer and releases said at least one drug at a pH of 3 through 6;
wherein said core comprises a concentration of said at least one drug of from 55-60%, said first inner layer coating comprises a percentage of coating agent of between 12.3-48.7%, and said second inner layer comprises a concentration of said at least one drug of from 40-45% and a percentage of coating agent of between 31.6-49.9%, the ratio of weight between the core and the external layer comprises between 0.4-0.1.

37. A method for achieving the release of an orally administered drug in the small and large bowel which comprises administering an oral pharmaceutical composition comprising a core, a first inner layer coating on the core, a second inner layer coating on the first inner layer coating wherein the core, the first inner layer coating and the second inner layer coating contain at least one drug, said at least one drug consisting of one or several drugs, either in combination and dispersed throughout each inner layer, or with separate drugs in the core, the first inner layer and the second inner layer, and the first inner layer coating comprises a coating agent consisting essentially of acrylic resin and releases said at least one drug at a pH of 5 through 8, and the second inner layer coating comprises a coating agent consisting essentially of a cellulose derivative, polyvinyl acetate phthalate, or polyvinyl acetate phthalate mixed with a plasticizer and releases said at least one drug at a pH of 3 through 6;
wherein said core comprises a concentration of said at least one drug of from 20-60%, said first inner layer coating comprises a concentration of said at least one drug of from 15-45% and a percentage of coating agent of between 12.3-48.7%, and said second inner layer comprises a concentration of said at least one drug of from 15-45% and a percentage of coating agent of between 31.6-49.9%.

38. The method according to claim 37, wherein the composition is in the form of a tablet.

39. The method according to claim 37, wherein the first inner layer coating releases said at least one drug at a pH of 6 through 8 and the second inner layer coating releases said at least one drug at a pH of 4 through 6.

40. The method according to claim 37, wherein the acrylic resin comprises a polyacrylate.

41. The oral pharmaceutical composition according to claim 40, wherein the polyacrylate is selected from the group consisting of polymethacrylate, polyethylacrylate, polymers of methacrylic acid, copolymers of methacrylic acid, terpolymers of methacrylic acid, polymers of methyl methacrylate, copolymers of methyl methacrylate, terpolymers of methyl methacrylate, polymers of trimethylammonium ethyl methacrylate chloride, copolymers of trimethylammonium ethyl methacrylate chloride, terpolymers of trimethylammonium ethyl methacrylate chloride, their derivatives, and mixtures thereof.

42. The method according to claim 37, wherein the cellulose derivative comprises ethylcellulose.

43. The method according to claim 42, wherein the cellulose derivative is hydroxypropylmethylcellulose.

44. The method according to claim 37, wherein said at least one drug is useful for treating an intestinal diseases.

45. The product produced by the method of claim 37.

46. A method for treating an intestinal disease orally which comprises administering an oral pharmaceutical composition, effecting delivery of drug to both the small and large bowel, comprising a core, a first inner layer coating on the core, a second inner layer coating on the first inner layer coating, wherein the core, the first inner layer coating and the second inner layer contain at least one drug, said at least one drug consisting of one or several drugs, either in combination and dispersed throughout each inner layer, or with separate drugs in the core, the first inner layer and the second inner layer, and the first inner layer coating comprises a coating agent consisting essentially of acrylic resin nd releases said at least one drug at a pH of 5 through 8, and the second inner layer coating comprises a coating agent consisting essentially of a cellulose derivative, polyvinyl acetate phthalate, or polyvinyl acetate phthalate mixed with a plasticizer and releases said at least one drug at a pH of 3 through 6;
wherein said core comprises a concentration of said at least one drug of from 20-60%, said first inner layer coating comprises a concentration of said at least one drug of from 15-45% and a percentage of coating agent of between 12.3-48.7%, and said second inner layer comprises a concentration of said at least one drug of from 15-45% and a percentage of coating agent of between 31.6-49.9%.

47. A method for the treatment of mammals by the oral administration of a therapeutically active dose of a drug, comprising administering a pharmaceutical composition effecting delivery of at least one drug to both the small and large bowel comprising ac ore, a first inner layer coating on the core, and a second inner layer coating on the first inner layer coating, said at least one drug consisting of one or several drugs, either in combination and dispersed throughout each inner layer, or with separate drugs in the core, the first inner layer and the second inner layer, wherein the core, the first inner layer coating, and the second inner layer coating contain a drug, and the first inner layer coating comprises a coating agent consisting essentially of acrylic resin and releases said at least one drug at a pH of 5 through 8, and the second inner layer coating comprises a coating agent consisting essentially of a cellulose derivative, polyvinyl acetate phthalate, or polyvinyl acetate phthalate mixed with a plasticizer and releases said at least one drug at a pH of 3 through 6;

wherein said core comprises a concentration of said at least one drug of from 20-60%, said first inner layer coating comprises a concentration of said at least one drug of from 15-45% and a percentage of coating agent of between 12.3-48.7%, and said second inner layer comprises a concentration of said at least one drug of from 15-45% and a percentage of coating agent of between 31.6-49.9%.

48. The method according to claim 47, wherein the mammals include a human.

49. A method of making an oral pharmaceutical composition effecting delivery of at least one drug to both the small and large bowel comprising the steps of:

(i) mixing at least one drug and a pharmaceutically acceptable excipient and comprising the mixture to form a core;

(ii) mixing the components of a first inner layer coating comprising a first coating agent and at least one drug and applying the first inner layer coating to the core;

(iii) drying the coating core;

(iv) mixing the components of a second inner layer coating comprising a second coating agent and at least one drug and applying the second inner layer coating to the once coated core; and (v) drying the twice coated core; wherein the first inner layer coating comprises a coating agent consisting essentially of acrylic resin and releases said at least one drug at a pH of 5 through 8, and the second inner layer coating comprises a coating agent consisting essentially of a cellulose derivative, polyvinyl acetate phthalate, or polyvinyl acetate phthalate mixed with a plasticizer and releases said at least one drug at a pH of 3 through 6, said at least one drug consisting of one or several drugs, either in combination or with separate drugs in the core, the first inner layer and the second inner layer;

wherein said oral pharmaceutical composition comprises a concentration of said at least one drug of from 20-60% in said core, a concentration of said at least one drug of from 15-45% and a percentage of coating agent of between 12.3-48.7% in said first inner layer, and a concentration of said at least one drug of from 15-45% and a percentage of coating agent of between 31.6-49.9% in said second inner layer.

50. The method according to claim 49, wherein the drug comprises salicylates, beclomethasone, indomethacin, steroids, salicylazosulphapyridine, pipenzolate bromide, silicium oxide, bismuth oxide, aluminum oxide, magnesium oxide, sodium oxide, digestive enzymes or a mixture thereof.

51. The method according to claim 49, wherein said at least one drug is useful for treating intestinal diseases.

52. The method according to claim 49, wherein said at least one drug is 5-amino salicylic acid.

53. The method according to claim 49, wherein the cellulose derivative is hydroxypropylmethylcellulose.

54. The method according to claim 49, wherein the cellulose derivative comprises ethylcellulose.

55. The product produced by the method of claim 49.

* * * * *